United States Patent [19]
Scheer et al.

[11] Patent Number: 5,659,388
[45] Date of Patent: Aug. 19, 1997

[54] METHOD AND APPARATUS FOR OPERATING A CONDENSATION NUCLEUS COUNTER WITH IMPROVED COUNTING STABILITY AND ACCURACY OVER A VARIABLE DETECTION THRESHOLD

[75] Inventors: Craig A. Scheer, Ceres; Bradley W. Scheer, San Jose, both of Calif.

[73] Assignee: VLSI Standards, Inc., San Jose, Calif.

[21] Appl. No.: 712,362

[22] Filed: Sep. 11, 1996

[51] Int. Cl.⁶ .................................................. G01N 1/00
[52] U.S. Cl. ............................................................ 356/37
[58] Field of Search ............................ 356/37, 336, 338, 356/339

[56] References Cited

U.S. PATENT DOCUMENTS

| | | | |
|---|---|---|---|
| 3,694,085 | 9/1972 | Rich | 356/37 |
| 3,806,248 | 4/1974 | Sinclair | 356/37 |
| 4,128,335 | 12/1978 | Haberl et al. | 356/37 |
| 4,449,816 | 5/1984 | Kohsaka et al. | 356/37 |
| 4,790,650 | 12/1988 | Keady | 356/37 |
| 4,792,199 | 12/1988 | Borden | 356/37 |
| 4,950,073 | 8/1990 | Sommer | 356/37 |
| 5,026,155 | 6/1991 | Ockovic et al. | 356/37 |
| 5,118,959 | 6/1992 | Caldow et al. | 250/573 |
| 5,239,356 | 8/1993 | Holländer et al. | 356/37 |

*Primary Examiner*—Richard A. Rosenberger
*Attorney, Agent, or Firm*—Thomas Schneck

[57] ABSTRACT

A condensation nucleus counter includes a saturator and a condenser with a thermoelectric device (TED) to simultaneously cool the condenser and heat the saturator. A controller is featured which operates the TED to maintain the temperature differential between the saturator and the condenser to within ±1.5° C. at steady state. The controller may be set by a user to operate at any desired setpoint temperature.

15 Claims, 6 Drawing Sheets

METHOD AND APPARATUS FOR OPERATING A CONDENSATION NUCLEUS COUNTER WITH IMPROVED COUNTING STABILITY AND ACCURACY OVER A VARIABLE DETECTION THRESHOLD

TECHNICAL FIELD

The present invention relates generally to detecting and counting particulate matter in an air sample, and more specifically to particulate detection using a condensation nucleus counter.

BACKGROUND OF THE INVENTION

Particulate monitoring in a clean environment is a crucial operation in semiconductor fabrication facilities. Particulate contamination causes many problems in the semiconductor manufacturing process. For example, yields may be significantly reduced by the presence of contaminants present on the surface of the wafer during manufacturing. If the number and size of airborne particles can be quantified, then a determination can be made as to the effect of different sized particles on the semiconductor process.

Current methods of counting airborne particles include laser particle counters (LPCs), scanning surface inspection systems (SSISs) for scanning wafers, and condensation nucleus counters (CNCs). The LPC is a laser based optical particle counter. A particle travels through a focused laser beam which produces scattered light at the detector which is converted to an electrical signal. The LPC typically is useful only for sizes larger than 0.200 µm. Newer LPCs, however, are capable of detecting particles to less than 0.100 µm, but they are bulkier and are more costly to acquire. Moreover, even the newer LPCs will not suffice for next generation semiconductor processes which will achieve submicron line widths, where particle sizes on the order of 0.050 µm will be significant.

Surface inspection systems for wafer scanning are expensive. They tend to be impractical in a manufacturing environment due to the long data collection times necessary to adequately collect particle information for the wafer. In addition, there are problems with skewed data results, since larger particles on the wafer tend to be counted with greater efficiency than smaller particles. The distribution of particle sizes is further skewed if the effects of the impaction of larger particles are taken into account. The smaller particles are kept off the surface by a hydrodynamic boundary layer and therefore follow the streamlines around the wafer.

A condensation nucleus counter offers good low end particle resolution, and at the same time can be used for particle sizes larger than 3 µm. The principle behind a CNC is the same as the LPC, but the particles in a CNC are first subjected to a heterogeneous condensation step, whereby the particles are "grown" to sizes on the order of 5–7 µm. By so doing, the particle diameters are large enough to be efficiently counted.

For a given saturation ratio, the vapor can only condense onto a particle which is large enough to serve as a nucleation point. The degree of supersaturation is measured by its saturation ratio. The saturation vapor pressure is defined as the equilibrium partial pressure for a liquid surface at a given temperature. This minimum particle size acting as a nucleation source is called the Kelvin diameter, and is shown by the relationship:

$$\text{saturation ratio} = \frac{P}{P_s} = \exp\frac{4gM}{rRTd}$$

where:

P is the vapor pressure of the condensing fluid;
$P_s$ is the saturation vapor pressure at temperature, T;
g is the surface tension of the condensing fluid;
M is the molecular weight of the condensing fluid;
r is the density of the condensing fluid;
R is the universal gas constant;
T is the absolute temperature; and
d is the Kelvin diameter.

The Kelvin diameter is significant only for particles less than 0.1 µm. The larger the saturation ratio, the smaller the Kelvin diameter. A large saturation ratio will also cause the particle to grow. The above equation is important since the saturation ratio is dependent upon the differential setpoint temperature. For every droplet size, there is one saturation ratio that will exactly maintain that size particle; too great a saturation ratio and the particle grows; too small and it evaporates. Conversely, for a given saturation ratio only those particles having a certain diameter (d) are stable; smaller particles evaporate, larger particles grow.

Basically, a CNC consists of a saturator containing a bath of condensing fluid, through which an air sample is passed. The air sample, being saturated with vapors from the bath, is then passed through a condenser. By setting the temperature of the condenser to be less than that of the saturator, the vapors in the saturated air sample condense onto individual particles suspended in the air sample, thus enlarging the particles to form droplets. The droplets are then detected by optical means, and counted. The temperature differential between the saturator and the condenser is referred to as the differential setpoint temperature.

While CNCs are capable of detecting particles as small as 0.02 µm, the droplets which form in the condensation chamber generally are uniform in size regardless of the sizes of the particles. Thus, it is not possible to ascertain the sizes of the original particles. Nevertheless, it may be desirous to change the detection limit; for example, to exclude the smallest particles (<0.05 µm) which are not yet a concern in semiconductor fabrication. To achieve a different detection limit, external components are relied upon. Two widely used components are diffusion batteries and inertial impactors, which serve as particle size selectors.

A diffusion battery consists of a series of fine meshed screens contained in a housing that determines the threshold size of the CNC (likened to an electrical high pass filter). The diffusion battery is placed in the aerosol inlet of the CNC to raise the lower limit of detectable particle size. The diffusion battery separates particles according to their diffusion coefficients. It eliminates small particles by Brownian motion and passes the larger particles. Besides requiring periodic maintenance, the efficiency curve as a function of particle size is not very steep.

Inertial impactors are another source for size discrimination, but are used for eliminating larger sized particles. A shortcoming of inertial impactors is particle bounce, wherein particles bounce off an impaction stage and get re-entrained in the flow stream. Particle bounce also increases as a function of flow rate for a given particle size. A method of minimizing particle bounce is to apply a layer of grease on the impaction stage. This approach, however, is not suited for the ultra-clean environments required of semiconductor fabrication facilities. An inertial impactor can be used in combination with a diffusion battery to operate a CNC for detection of particles within a range of sizes, but with the above-described limitations.

The setpoint temperature of conventional CNCs is maintained by measuring the actual temperature differential between the saturator and condenser. The temperature of the saturator and/or the condenser is then adjusted by an amount directly proportional to the amount of deviation from the setpoint temperature. For example, commercially available CNCs typically employ a thermoelectric device to transfer heat from the condenser to the saturator. The setpoint is maintained first by determining the difference between the measured differential temperature and the setpoint temperature. This difference, referred to as an error term, may be used directly as a control signal to operate the thermoelectric device. Alternatively, the error term may be reduced by a certain amount, e.g. divided by a constant factor, to obtain the correction signal.

The foregoing methods of maintaining the setpoint temperature lead to oscillations in the actual temperature differential ($\Delta T$) between the saturator and condenser, as can be seen in the graph of FIG. 3. It has been observed that variations in the actual temperature differential can be greater than $\pm 1.5°$ C. about the setpoint temperature.

It has been further observed that when the $\Delta T$ fluctuates, so does the number of particles counted. This is dramatically illustrated in the graph of FIG. 3, showing both the $\Delta T$ fluctuations and the particle count variations over time. The $\Delta T$ is shown by a solid line, and the particle count is shown by a dotted line. Data for the graph was taken after the CNC reached steady state conditions, roughly fifty minutes, as shown by the time scale. The particle source consisted of 0.100 µm particles at a constant aerosol concentration of 100 particles per second detected at varying $\Delta T$s.

When the $\Delta T$ varies by plus or minus one degree from a setpoint of 12° C., the particle counts vary from about zero (0) particles counted per second to 500 particles counted per second. Such variations in counted particles pose a tremendous problem in ascertaining an accurate level of air purity in a modern clean room.

Interestingly enough, there is no indication in the prior art which recognizes the problem of temperature fluctuations about the setpoint temperature. Prior art patents relating to CNC technology relate to CNC devices, improvements in the hardware, and enhanced functionality; and not to performance of the CNC. For example:

U.S. Pat. Nos. 3,806,248, 4,293,217, and 4,790,650 each discloses a portable CNC capable of providing continuous on-line operation.

U.S. Pat. No. 4,128,335 relates to a CNC apparatus for counting particles by taking multiple measurements and discarding those measurements in excess of an arbitrarily selected value.

U.S. Pat. No. 4,449,816 describes a continuous operation CNC featuring a design that avoids aerosol particle deposition on the wall surface of the cooling nozzle.

U.S. Pat. No. 4,792,199 discloses a CNC capable of monitoring extremely small particles in low pressure environments in real-time.

U.S. Pat. Nos. 4,950,073 and 5,026,155 each relates to an apparatus for counting particles of different sizes.

U.S. Pat. No. 5,118,959 discloses a CNC capable of avoiding water contamination of the working fluid.

U.S. Pat. No. 5,239,356 describes a CNC having multiple air flow paths.

An additional shortcoming of prior art CNC devices is that conventional CNCs require a considerable amount of time to reach steady state from a cold start, typically on the order of 40 minutes to one hour before particulate monitoring can begin.

What is needed is a condensation nucleus counter which exhibits a stable $\Delta T$ about a desired setpoint temperature, in order to ensure accurate particle counts. There is also a need for a CNC which exhibits a shortened warm-up time so that particulate monitoring can begin without requiring an operator to wait for the system to stabilize. There is need to provide a CNC which can detect and count different ranges of particle sizes without having to employ filtering devices such as diffusion batteries and inertial impactors, and which can quickly adjust to the new settings.

SUMMARY OF THE INVENTION

Like other condensation nucleus counters (CNC) of the prior art, the present invention includes a saturator section, a condensation chamber and a detection chamber. However, the present invention is distinguished by a controller cascaded in series with the CNC, and having a feedback path. The controller provides a control input to a thermoelectric device which extracts heat from the condensation chamber and transfers the heat to a heat sink. The heat sink is in thermal contact with the saturator, and thus serves to heat the saturator. Parameters of the controller are accessible by the user, allowing the user to tune the system, if needed.

The setpoint temperature of the CNC of the present invention is not fixed, but rather can be specified by the user. In addition, the controller of the present invention is capable of maintaining a temperature differential ($\Delta T$) between the saturator and the condenser to within $\pm 0.1°$ C. of a specified setpoint temperature. The $\Delta T$ of the CNC is substantially unaffected by external disturbances typically encountered in cleanroom settings. For example, a sudden change in ambient room temperature caused by a fan turning on or off is quickly compensated for by the CNC, thus holding the CNC to the desired setpoint temperature.

In addition, the CNC of the present invention reaches steady state in a much shorter time as compared to prior art devices. For example, FIG. 4 shows that the present invention CNC can attain a setpoint of 12.1° C. roughly within five minutes, at time A. FIG. 4 also shows the system's quick response to changes in the setpoint. Thus, at time C the setpoint is changed from 12.1° C. to 18.1° C. The CNC reaches steady state at 18.1° C. in approximately four minutes, at time C'. Conversely, when the setpoint is set back to 12.1° C. at time D, the CNC reaches steady state in about five to seven minutes, at time D'.

The graph of FIG. 4 further shows the CNC operating well within 0.1° C. of the setpoint temperature for the entire 200 minutes of operation. Setpoint stability in the present invention system is maintained even when a fan is turned on at time B, and subsequently turned off at time B' roughly fifteen minutes later.

Noteworthy is the minimal overshoot and undershoot of the $\Delta T$ as the system compensates for the sudden change in ambient when the fan is turned on and later turned off. This indicates a highly damped system. The high degree of damping is further evidenced by the minimal overshoot of the system at time C', when the higher setpoint (18.1° C.) is reached. More significantly, is the combination of high damping and a fast settling time of the system. Thus, at time A, the system requires roughly five minutes to warm up. Similarly, at times C' and D', the system quickly reaches the new setpoints with minimal overshoot and undershoot.

The ability for a user to select a setpoint obviates the need for external filters such as diffusion batteries and inertial impactors. This is highly advantageous in that the operator needs not shut the system down to install additional equipment. The quick response time to a new setpoint further enhances the usefulness of a user selectable setpoint.

BEST MODE OF CARRYING OUT THE INVENTION

Figure 1:
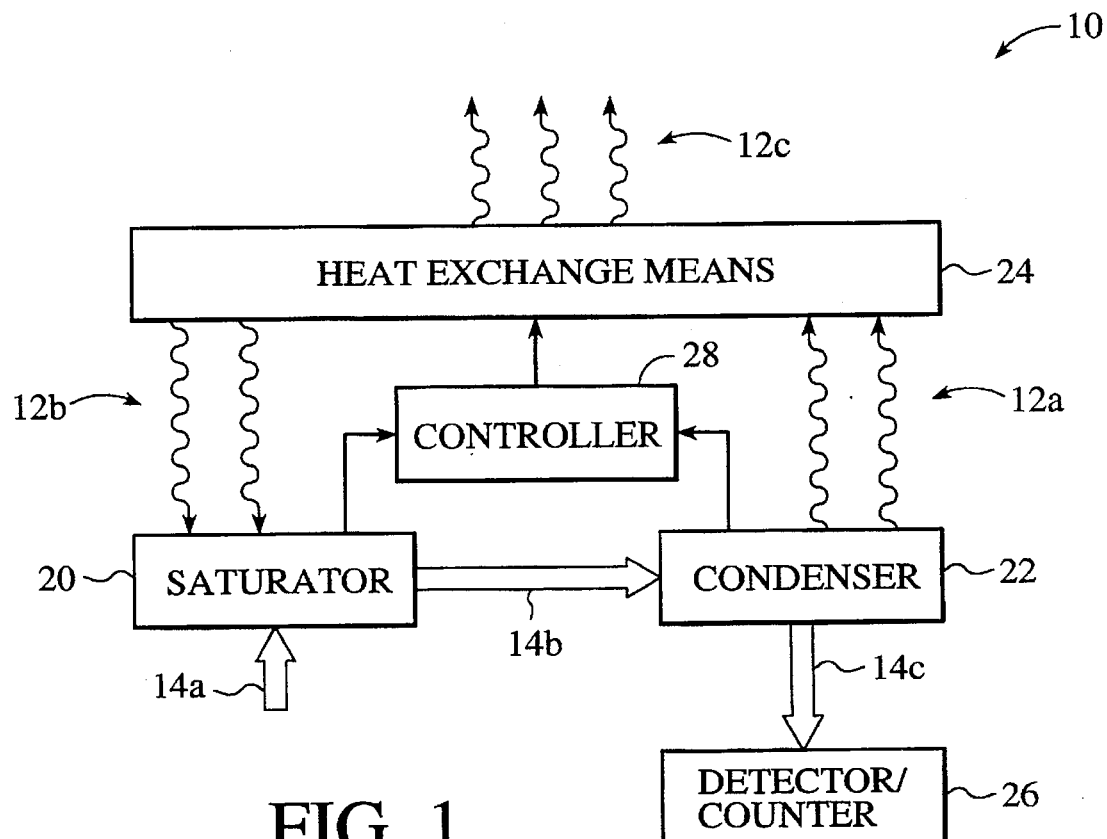
FIG. 1 is a schematic diagram of the condensation nucleus counter of the present invention.

As shown in FIG. 1, a condensation nucleus counter (CNC) 10 in accordance with the present invention includes a saturator 20, a condenser 22 and a heat exchange means 24. The schematic representation of FIG. 1 shows that thermal energy (heat) 12a is transferred from the condenser 22 to the heat exchange means 24. Some of the thermal energy is dissipated 12c to the surrounding environment, and some is transferred 12b to the saturator 20. A controller 28 receives temperature data from the saturator 20 and condenser 22. Based on this information, the controller outputs a signal to operate the heat exchange means, thus controlling the amount of thermal energy being transferred from the condenser to the saturator. An air flow path 14a–14c begins in the saturator 20, proceeds through the condenser 22, and is directed to a detector/counter 26.

Figure 2:
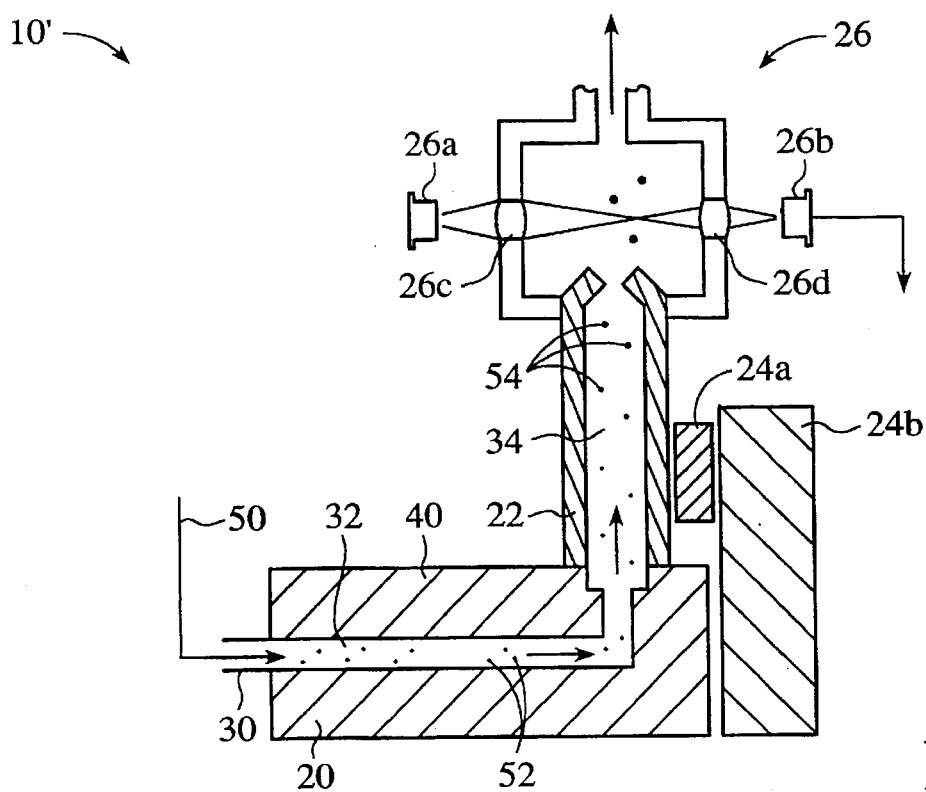
FIG. 2 shows a cutaway view of a condensation nucleus counter.
Figure 3:
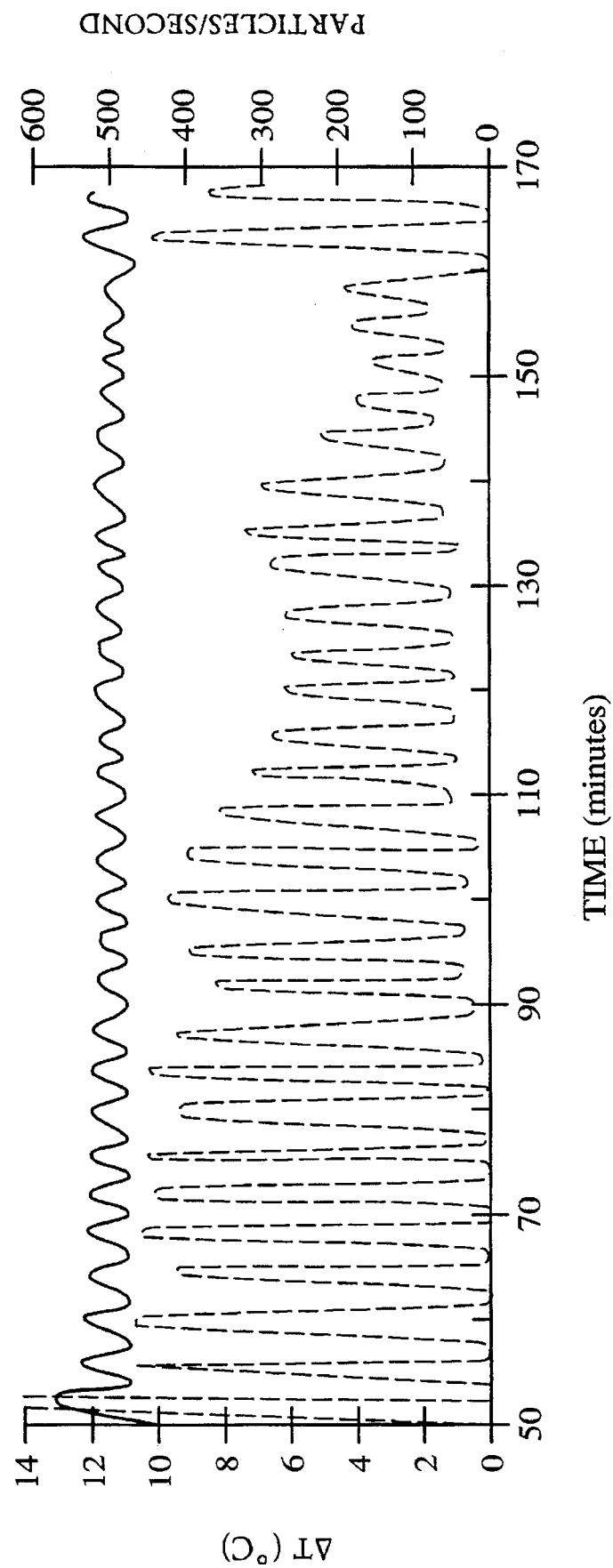
FIG. 3 is a graph showing the fluctuation in particle counts as a function of the system setpoint.

Turn now to the CNC 10' shown in FIG. 2. The saturator 20 consists of a porous block of material, immersed or filled with a working fluid 40. A typical working fluid is a perfluorinated hydrocarbon fluid available from Air Products and Chemicals, Inc. (Allentown, Pa.), available under the tradename Multifluor APF-175. Although the specific kind of fluid used is not critical in the present invention, APF-175 is especially well suited for use in a CNC because the fluid is non-toxic, non-flammable, and odorless. Another equally effective working fluid is supplied by 3M Corp., under the trademark Fluorinert®. Continuing, an air stream 50 containing suspended particles 52 enters the saturator 20 through an air inlet 30. From there, the air stream passes through a saturation region 32 within the saturator 20. The temperature of the working fluid 40 is heated above ambient, causing the air stream to become saturated with vapors of the fluid as the air flows through the saturation region 32.

The condenser 22 is in fluid communication with the saturator 20. The saturation region 32 opens into a condensation chamber 34 within the condenser. The temperature in the condensation chamber 34 is lower than ambient. As the saturated air stream exits the saturator 20 and enters the chamber, the fluid vapors in the air stream begin to condense on the particles 52 suspended in the air stream. The resulting aerosol droplets 54 which form are larger than the bare particles.

The air stream, which now includes droplets 54 of condensed vapor, continues into the detector 26. There, an LED laser 26a produces laser light which is focused by a lens 26c and directed into the chamber of the detector 26. The droplets 54 entering the detection chamber scatter the laser light. The scattered light is collected by another lens 26d and focused onto a photodetector 26b. The photodetector outputs an electrical pulse which is then registered by a counter (not shown). Thus, while the bare particles 52 in the air stream 50 are not detectable by the detector 26, the larger droplets 54 are of sufficient size for detection.

In a preferred embodiment, the heat exchange means 24 shown in FIG. 1 consists of a thermoelectric device (TED) 24a and a heat sink 24b as shown in FIG. 2. The thermoelectric device 24a is sandwiched between the condenser 22 and the heat sink 24b. The heat sink is in physical and thermal contact with the saturator 20. The thermoelectric device 24a is a solid state device which utilizes the Peltier effect, and so operates as a heat pump to transfer heat from the condenser 22. Specifically, heat energy at the TED/condenser junction is absorbed by electrons as they pass from the p-type material of the TED 24a (lower energy level) to the n-type material. An external power source (not shown) provides the energy to move the electrons in this manner. At the TED/heat sink junction, as the electrons move from the high energy state in the n-type material to the low energy state in the p-type material, the energy is absorbed as heat by the heat sink 24b. From the heat sink, most of the heat is dissipated into the surrounding environment. A portion of the heat, however, is conducted through the body of the heat sink 24b and absorbed by the saturator 20. In this way, the TED 24a serves to cool the condenser 22 while at the same time heating up the saturator 20. This simultaneous cooling and heating helps to minimize the response time of the system.

The temperature differential between the saturator and the condenser is referred to as the $\Delta T$ of the CNC. Under typical operating conditions, it is desirous to maintain the $\Delta T$ at a specific value; this specific value is known as the setpoint temperature. The task of maintaining the $\Delta T$ of the system at the setpoint temperature belongs to the controller 28, FIG. 1. The controller 28 has two inputs, each is a temperature measurement from either the saturator 20 or the condenser 22. The controller generates a control signal to operate the thermoelectric device 24a (FIG. 2) in response to the measured temperature differential ($\Delta T$).

Figure 5:
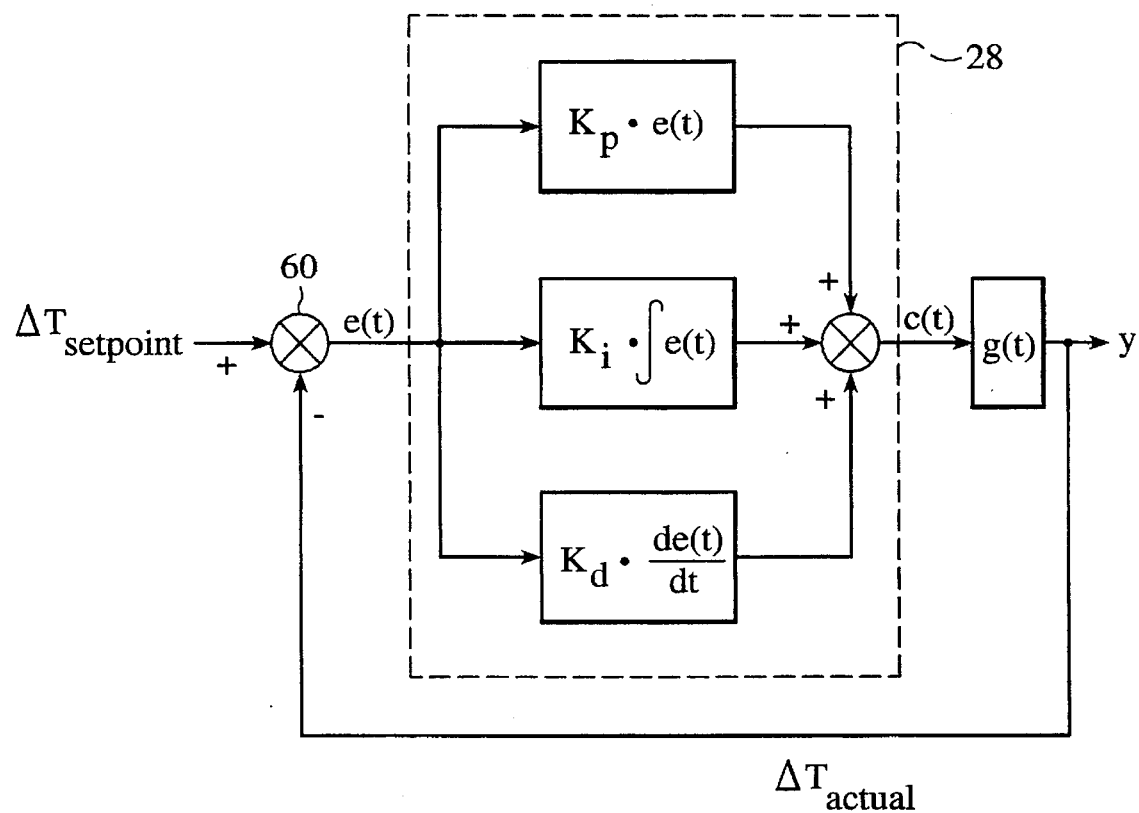
FIG. 5 is a time-domain representation of the system block diagram of the present invention.

The discussion will now focus on the controller 28 with reference to the block diagram of FIG. 5. The controlled system, namely the saturator 20, condenser 22, and heat exchange means 24, is represented by the block identified as g(t). The actual temperature difference $\Delta T_{actual}$ between the saturator 20 and the condenser 22 is the output y produced by the system. The open loop response of the CNC to a step input is g(t), the step input being a constant control signal which operates the TED 24a (FIG. 2) to produce a given $\Delta T$.

Continuing with FIG. 5, the system includes a unity feedback loop of the output y (namely, $\Delta T_{actual}$), which is fed back to a summing junction 60. The summing junction compares $\Delta T_{actual}$ against a desired setpoint temperature, $\Delta T_{setpoint}$. The result of the comparison is an error signal e(t), which is then fed into the controller 28. The controller utilized in the present invention is a proportional, integral, derivative (PID) type controller in series cascade with the controlled system g(t). The output of the controller 28 is a control signal c(t) which operates the TED 24a (FIG. 2). In the preferred embodiment, the controller 28 is implemented in software using the approximation methods of discrete Z-transforms to perform the computations. The saturator and condenser temperatures are sampled and converted to digital form. The firmware-based PID controller then computes a value for the control signal c(t) which operates the TED 24a. The control signal c(t) is an eight bit quantity, and ranges from zero (TED is turned off) to 255 (TED is fully on).

The proportional element $K_p$ of the controller 28 is effective in reducing errors arising from external disturbances which affect the temperatures of the saturator and condenser, but is not as effective in maintaining a steady state condition. The integral term $K_i$ therefore is needed to reduce steady state error. The derivative term $K_d$ increases the damping and improves the stability of the system.

With respect to the derivative term, it has been observed that the open loop step response of the CNC includes some superimposed noise. This is an important observation for the derivative term. If the derivative of the error is taken at each sample period, the system would not be optimally controlled because the slope (and sign) of the derivative term would constantly change due to the superimposed noise, making it difficult to maintain a steady state condition. Thus, in accordance with the present invention, the derivative term is averaged over a certain sample period. The averaged derivative term is substituted for the derivative term shown in FIG. 5. For example, it has been found that an average over five samples provides sufficient smoothing of the derivative. It is noted, however, that the number of samples to be averaged is not critical, and may vary from system to system.

Since the CNC is an inherently slow thermal response system, the integral error tends to build up to a large value which could lead to unacceptable transient oscillations. This is known in the art as integral windup. Therefore, an anti-windup integrator must be incorporated in the controller 28, to leave the integral term unchanged during those times when the TED 24a is being operated at its limits and to resume integrating when the TED is within its operating limits.

Figure 6:
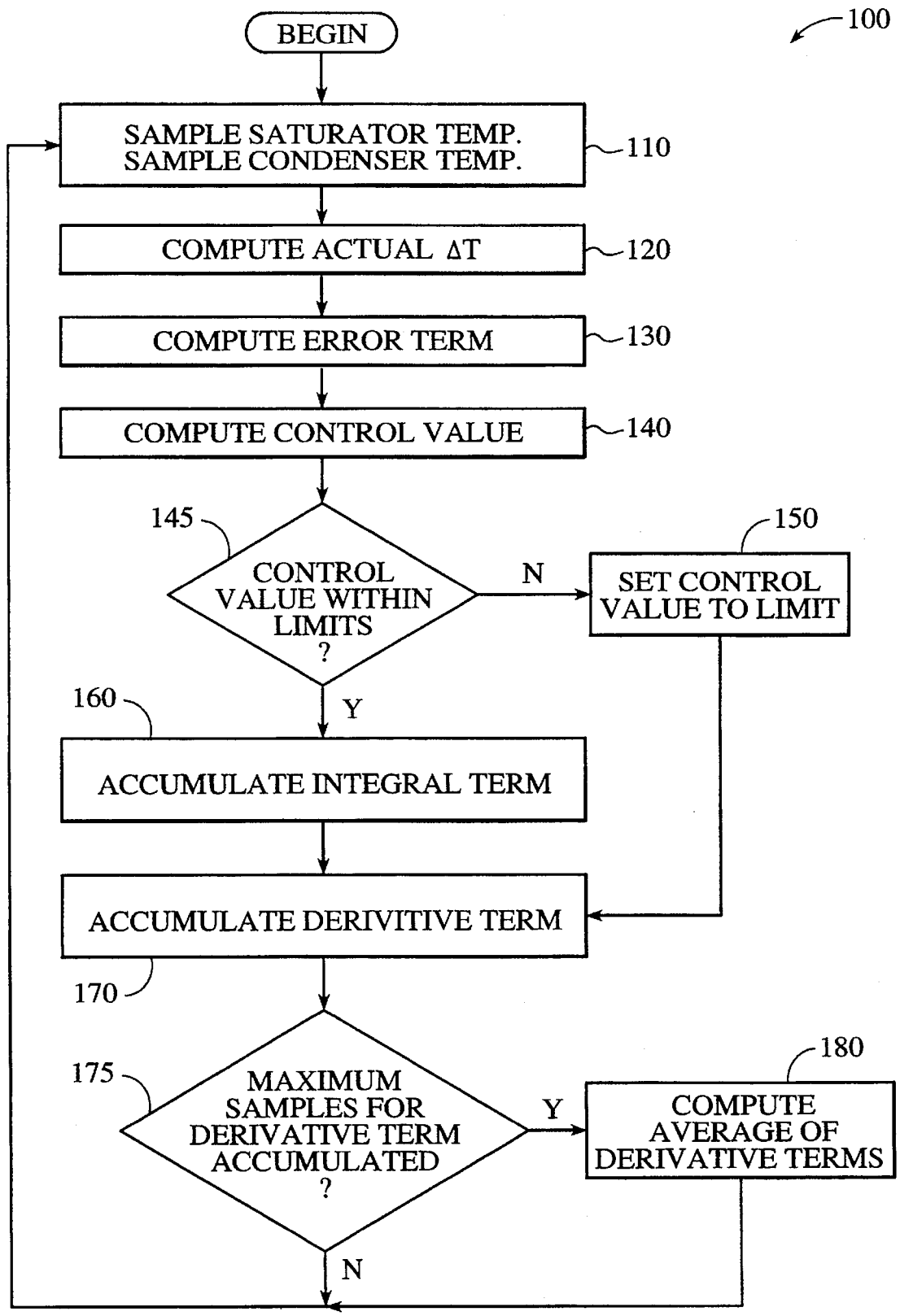
FIG. 6 is a flowchart of the controller of the present invention.

Refer now to FIG. 6 with respect to the operation of the controller in accordance with the present invention. First, the current saturator 20 and condenser 22 temperatures are sampled, step 110. The $\Delta T_{actual}$ value is computed as the difference between the saturator temperature and the condenser temperature, step 120. The error term is then computed as the difference between the desired setpoint temperature $\Delta T_{setpoint}$ and the actual $\Delta T$, step 130. The control signal is computed in accordance with the block diagram of the controller 28 shown in FIG. 5, step 140, recalling that an average of the derivative term is used. A check is made to determine whether the computed control signal is within the operating limits (0-255) of the TED 24a, step 145. If the control signal is within the operating limits, then the error is accumulated into the integral term, step 160. If the control signal exceeds the operating limits, the control signal is set to the minimum (0) or maximum (255) limit, step 150. Note that the integral term is not updated, thus avoiding integral windup. Continuing, the error term is accumulated in the derivative term, step 170. Finally, a check is made to determine whether the average derivative term needs to be updated, steps 175 and 180. As mentioned above, the criterion used in the preferred embodiment of the invention is to compute an average every five samples.

The following code fragment written in the C programming language illustrates a typical implementation of the flowchart in FIG. 6:

```
/* take sample of current temperatures, step 110 */
temp_sat = get_temp(SATURATOR);
temp_cond = get_temp(CONDENSER);
/* compute actual temperature differential, step 120 */
deltaT_actual = temp_sat - temp_cond;
/* compute error term, step 130 */
error = deltaT_setpoint - deltaT_actual;
/* compute control signal, step 140 */
control =
        Kp * error +
        Ki * integrated_error +
        Kd * averaged_differentiated_error;
/* anti-windup integration, steps 145, 150 and 160 */
    if( 0 < control )      /* set to min. limit, step 150 */
                           control = 0;
    else if                /* set to max. limit, step 150 */
    ( control > 255 )      control = 255;
    else                   /* integrate error term, step 160 */
                           integrated_error += error;
    /* differentiate the error term, step 170 */
    differentiated_error += error;
    /* update the averaged differential term, steps 175 and 180 */
    if( number_of_samples++ >= 5 )
    {
        averaged_differentiated_error = differentiated_error/5;
        differentiated_error = 0;
        number_of_samples = 0;
    }
```

The code fragment may be continuously executed in a loop, or may be contained within a subroutine that is periodically invoked from a higher level subroutine.

The software used in the present invention also includes accepting input from a user to specify the desired setpoint temperature for the purpose of selecting the minimum detectable particle size. It is presumed that the value for deltaT_ setpoint has been previously specified in this way. The ability for a user to select a setpoint obviates the need for external filters such as diffusion batteries and inertial impactors. This is highly advantageous in that the operator need not shut the system down to install additional equipment. The quick response time to a new setpoint further enhances the usefulness of a user selectable setpoint.

The discussion will now turn to the selection of the values for $K_p$, $K_i$, and $K_d$. The response of the system is mostly dependent on these variables. As a first approximation, one suggested method is to obtain the transfer function for the system and setting the variables to the coefficients of the denominator of the transfer function. This approach, however, is appropriate only for second order systems. The transfer function of the CNC is approximated as a first order system.

A widely accepted approach is known as the Zieglerl-Nichols tuning rules, which is based on stability analysis of the system. The integral and derivative constants, $K_i$ and $K_d$, are initially set to zero. The proportional constant $K_p$ then is increased from zero to a value until the system begins to oscillate. The constants are then computed as follows:

$$K_p = 0.6\ K_m,$$

where $K_m$ is the gain at which oscillation occurs $$K_i = \frac{K_p \omega_m}{\pi},$$

where $\omega_m$ is the oscillation frequency $$K_d = \frac{K_p \pi}{4\omega_m}$$

This method usually results in adequate parameters for a PID controller, but will not be optimal. The method does not take into account design characteristics such as transient response, overshoot, rise time, or settling time.

Contrary to these conventional approaches, the selection of the K factors in accordance with the present invention involves examining the Bode plot or root-locus plot of the system's transfer function, including the CNC device and the PID controller of the present invention. The constants are varied, and the effects of such variations on the Bode plot, for example, are examined. Thus, by repeating this process for various combinations of values for the K factors, the Bode or root-locus plots can be used to determine the combination of K factors which best minimizes the effects of overshoot, transient response time, and rise time. This method is greatly facilitated by the use of any one of the many commercially available mathematical analysis tools, such as MATLAB®.

Figure 4:
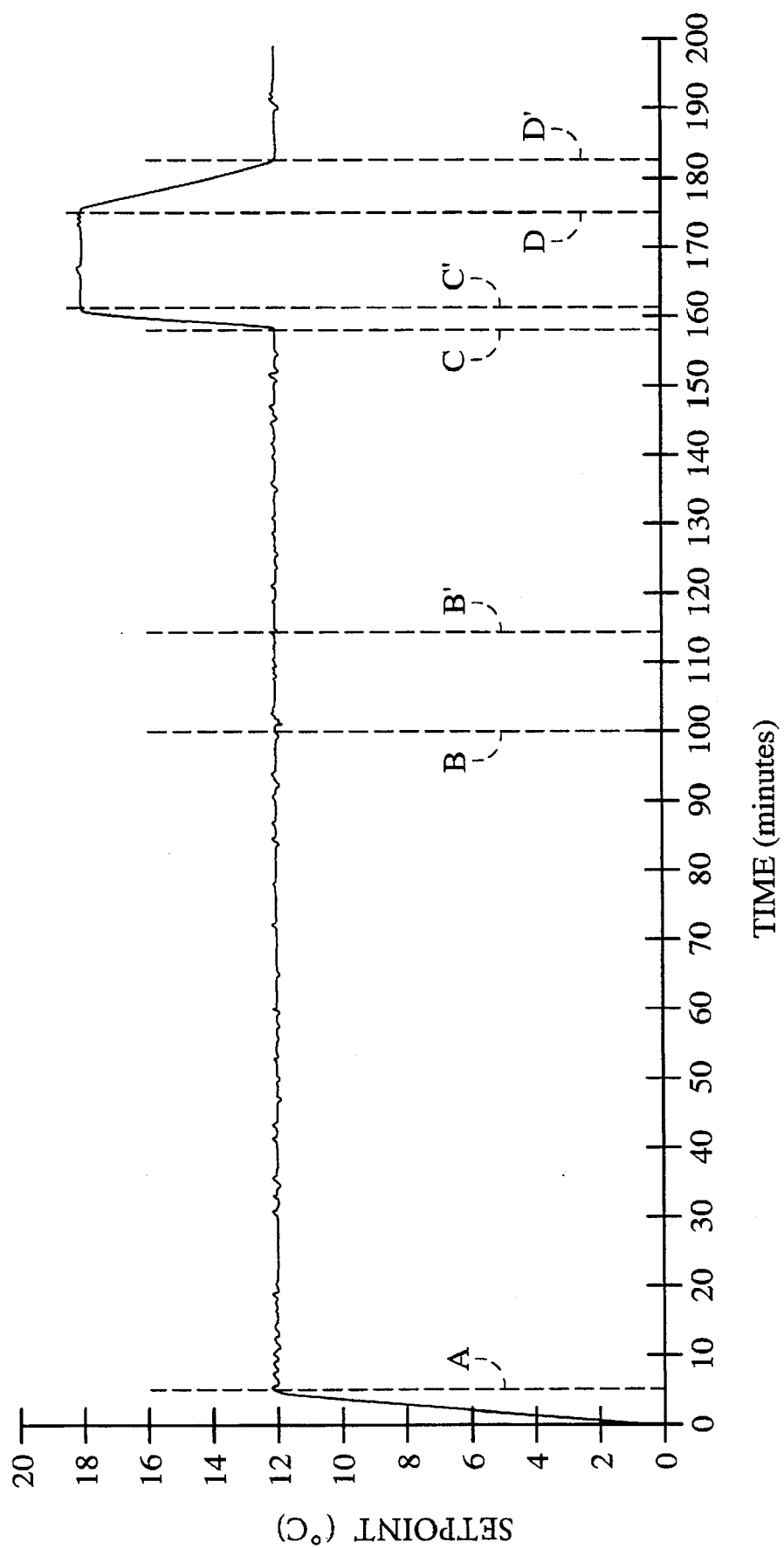
FIG. 4 is a graph showing the system time response of the CNC of the present invention.
Figure 7:
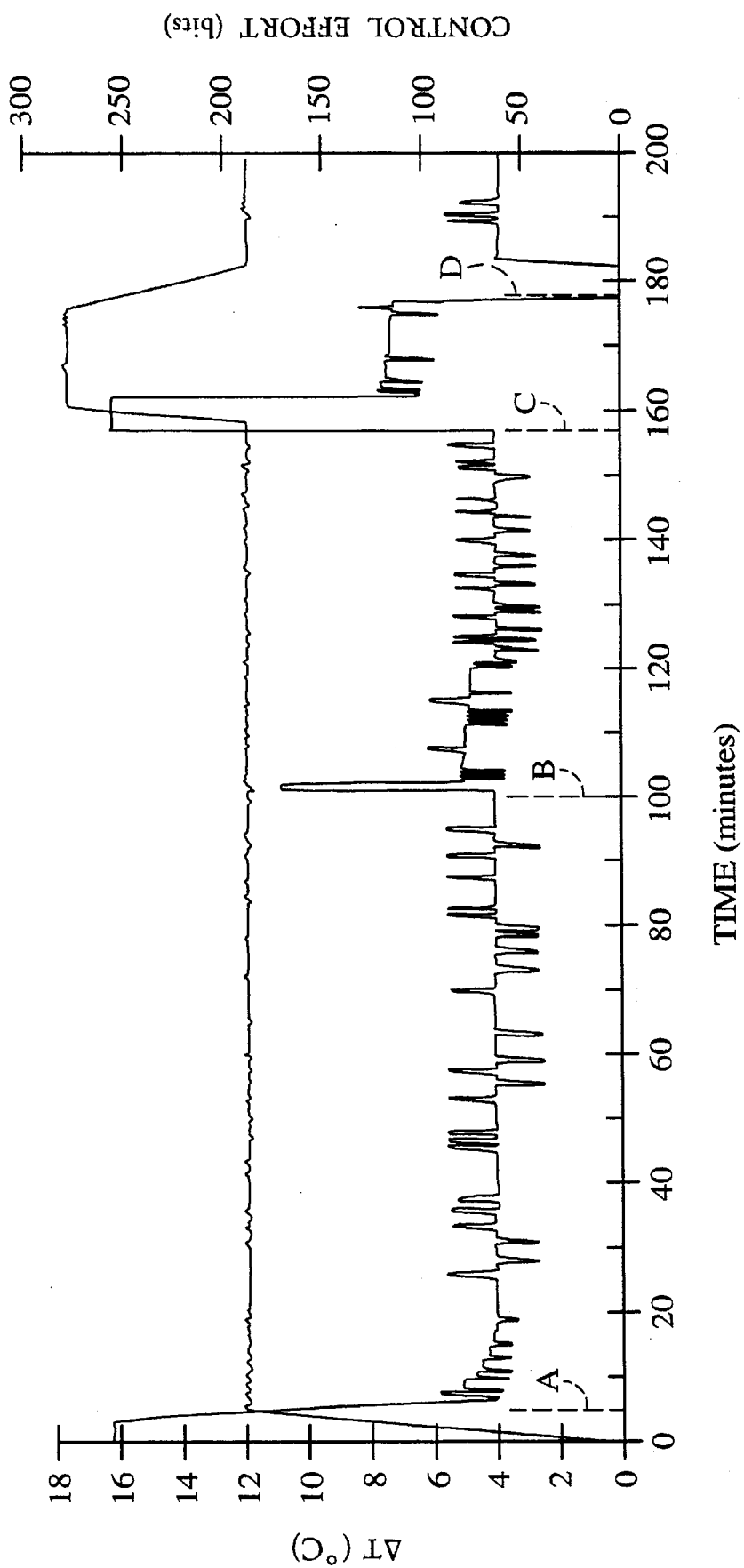
FIG. 7 is a graph of the system time response superimposed with a plot of the control effort exerted by the system of the present invention.

FIG. 7 duplicates the ΔT response plot of FIG. 4 with the addition of a plot of the control signal c (FIG. 5), showing the control effort exerted by the controller of the present invention. The vertical axis on the left shows the scale, in °C., for the ΔT plot. The vertical axis on the right side of the graph shows the scale for the plot of the control signal (control effort). Recall that the control signal is an eight bit quantity that is transmitted to the TED 24a, and so the units on the control signal scale are in bits (range: 0-255).

Beginning at time zero (0), the TED is fully on, as indicated by the maximum output of the control signal. By operating the TED with a 100% duty cycle, the saturator and condenser temperatures reach the setpoint ΔT (12.1° C.) in minimum time. At time A, when the setpoint ΔT is reached, the TED is operated at a much lower level. For the next 100 minutes, the control effort of the controller operates the TED roughly at a 25% duty cycle.

Recall from FIG. 4 that at time B a fan is turned on, thus introducing an external thermal disturbance to the system. The control effort jumps to a higher operating level to compensate for the disturbance, and increases the duty cycle of the TED to roughly 68%. The efficacy of the controller's effort in maintaining the setpoint temperature is reflected in the relatively flat ΔT curve.

At time C, the system is set to a new setpoint ΔT (18.1° C.). As can be seen in FIG. 7, the control effort of the controller once again is dramatically increased. This time, the TED is set to operate at maximum (100% duty cycle), with the result that the new ΔT is attained in minimum time. At time D, the system is set back to its original setpoint of 12.1° C. Once more, a dramatic change in the control effort is made. The TED is turned off for a period of time (0% duty cycle), to allow the saturator and condenser temperatures to quickly reach the lower setpoint.

We claim:

1. A method of counting particles in an air sample, comprising:

(a) selecting a desired setpoint temperature between a bath of working fluid and a condensation region;

(b) adjusting the temperature of said bath and the temperature of said condensation region so that the difference in temperatures is substantially equal to said desired setpoint temperature;

(c) passing said air sample through said bath to saturate said air with vapors of said working fluid;

(d) passing said saturated sample of air through said condensation region, thereby causing said vapors to condense on individual particles suspended in said saturated sample of air to form droplets;

(e) detecting said droplets; and (f) counting said detected droplets; said step of adjusting including substeps of:

(1) measuring the difference between the temperatures of said bath and said condensation region;

(2) integrating said measured difference;

(3) differentiating said measured difference;

(4) computing a control value based on said measured difference, said integration of said measured difference and said differentiation of said measured difference;

(5) changing the temperature of said bath by an amount proportional to said control value; and (6) changing the temperature of said condensation region by an amount proportional to said control value.

2. The method of claim 1 wherein said step of detecting includes illuminating said droplets with a laser, whereby said laser is scattered by said droplets and is detected thereby.

3. The method of claim 1 wherein said substep (5) includes transferring heat from said condensation region to said bath.

4. The method of claim 1 wherein said substep (4) includes computing:

$$K_P \cdot e(t) + K_i \int e(t) dt + K_d \frac{de(t)}{dt}$$

for selected values of $K_p$, $K_i$, and $K_d$.

5. The method of claim 4 further including a step of selecting values for $K_p$, $K_i$, and $K_d$ comprising:

determining a transfer function which models the effect upon said measured difference between the temperatures of said bath and said condensation region in response to said step of adjusting the temperature of said bath and said condensation region;

assigning values for each of $K_p$, and $K_i$, and $K_d$;

plotting a root-locus or a bode plot of said transfer function; and repeating said steps of assigning and plotting for different values of $K_p$, $K_i$, and $K_d$ to minimize overshoot, transient response, and rise time characteristics of said transfer function.

6. A condensation nucleus counter comprising:

a reservoir of volatile fluid having an air inlet for directing a sample of air through said volatile fluid to saturate said air sample with vapors of said volatile fluid;

a condensation chamber disposed downstream of and in fluid communication with said reservoir to condense said vapors on individual particles suspended in said air sample, thereby encapsulating said particles;

a droplet counter disposed downstream of and in fluid communication with said condensation chamber, for detecting and counting said encapsulated particles;

means for selecting a desired temperature differential between said reservoir and said condensation chamber, so that condensation occurs only on particles of a certain size;

means for measuring a current temperature differential between said reservoir and said condensation chamber;

a heat exchange means for transferring heat between said reservoir and said condensation chamber, said heat exchange means having a control input to control the amount of heat transferred;

means for generating a control signal including means for computing an error signal, said error signal being proportional to the difference between said current and desired temperature differentials, said means for generating further including means for computing said control signal as a function both of said error signal and an integral of said error signal; and means for applying said control signal to said control input, thereby controlling said heat exchange means to maintain said current temperature differential substantially equal to said desired temperature differential.

7. The condensation nucleus counter of claim 6 wherein said heat exchange means includes a thermoelectric device and a heat sink, said thermoelectric device physically coupled to said condensation chamber and to said heat sink, said heat sink physically coupled to said reservoir.

8. The condensation nucleus counter of claim 6 wherein said means for computing said control signal includes computing:

$$K_p e(t) + K_i \int e(t) dt.$$

9. The condensation nucleus counter of claim 8 further including user input means for assigning a value to each of $K_p$ and $K_i$.

10. The condensation nucleus counter of claim 6 wherein said control signal further is a function of the differential of said error signal.

11. The condensation nucleus counter of claim 10 wherein said means for computing said control signal includes computing:

$$K_P \cdot e(t) + K_i \int e(t) dt + K_d \frac{de(t)}{dt}.$$

12. The condensation nucleus counter of claim 11 further including user input means for assigning a value to each of $K_p$, $K_i$ and $K_d$.

13. A method of maintaining a desired setpoint of a condensation nucleus counter, said condensation nucleus counter having a fluid reservoir, a condenser in fluid communication with said fluid reservoir and a thermoelectric couple for heat transfer between said condenser and said fluid reservoir, said method comprising:

(a) ascertaining a temperature differential between said fluid reservoir and said condenser;

(b) computing an error term as the difference between said desired setpoint and said measured temperature differential;

(c) computing a running sum of said error term;

(d) computing an average of the current value of said error term and at least one previous value of said error term;

(e) computing a control term as the sum of said error term, said running sum, and said average term;

(f) adjusting said thermoelectric couple on the basis of said control term, whereby an amount of heat is transferred from said fluid reservoir to said condenser; and (g) repeating steps (a) through (f), thereby attaining and maintaining said desired setpoint.

14. The method of claim 13 further including a step of selecting first, second, and third constants, prior to said step (a); said step of computing a control term including multiplying said error term by said first constant, multiplying said running sum by said second constant, and multiplying said average term by said third constant, thereby implementing a PID controller; said step of selecting first, second, and third constants including:

(i) ascertaining a transfer function of a system having said PID controller in series cascaded with said condensation nucleus counter, and further having unity feedback;

(ii) varying first, second, and third constants of said PID controller;

(iii) computing, based on said transfer function, a root-locus plot or a Bode plot of said system; and (iv) repeating said substeps (ii) and (iii) until a combination of selected values of said first, second, and third constants is found which minimizes overshoot, transient response, and rise time of said system.

15. The method of claim 13 further including limiting said control term to a minimum value and a maximum value, said running sum being computed only if said computed control term is less than or equal to said maximum value and greater than or equal to said minimum value.

* * * * *